United States Patent
Samaniego et al.

(10) Patent No.: US 10,706,539 B2
(45) Date of Patent: Jul. 7, 2020

(54) SUBTRACTION ALGORITHM FOR DETECTION OF TUMORS

(71) Applicant: RAYTHEON COMPANY, Waltham, MA (US)

(72) Inventors: Raymond Samaniego, Prosper, TX (US); Lauren G. Hatchell, Dallas, TX (US); Tuan T Tran, Plano, TX (US); John L. Tomich, Coppell, TX (US); Bryan D. Anderson, Mckinney, TX (US)

(73) Assignee: RAYTHEON COMPANY, Waltham, MA (US)

( * ) Notice: Subject to any disclaimer, the term of this patent is extended or adjusted under 35 U.S.C. 154(b) by 87 days.

(21) Appl. No.: 16/102,449

(22) Filed: Aug. 13, 2018

(65) Prior Publication Data

US 2019/0050986 A1      Feb. 14, 2019

Related U.S. Application Data

(60) Provisional application No. 62/545,410, filed on Aug. 14, 2017.

(51) Int. Cl.
*G06K 9/00*          (2006.01)
*G06T 7/00*          (2017.01)
(Continued)

(52) U.S. Cl.
CPC ............. *G06T 7/0012* (2013.01); *G06T 5/50* (2013.01); *G06T 7/0016* (2013.01); *G06T 7/11* (2017.01); *G06T 7/40* (2013.01); *A61B 6/032* (2013.01); *A61B 6/481* (2013.01); *A61B 6/5205* (2013.01); *G06T 2207/10076* (2013.01); *G06T 2207/10081* (2013.01); *G06T 2207/20221* (2013.01);
(Continued)

(58) Field of Classification Search
None
See application file for complete search history.

(56) References Cited

U.S. PATENT DOCUMENTS 6,111,975 A * 8/2000 Sacks .................... G06T 5/20
                                                       382/103
6,760,611 B1   7/2004 Watanabe
(Continued)

FOREIGN PATENT DOCUMENTS

DE   10 2010 041 619 A1   3/2012
JP   2004-312434 A        11/2004

OTHER PUBLICATIONS

Co-Pending U.S. Appl. No. 15/489,652 entitled System and Method for Combining 3D Images in Color, filed Apr. 17, 2017, allowed Jun. 8, 2018.
(Continued)

*Primary Examiner* — Shervin K Nakhjavan
(74) *Attorney, Agent, or Firm* — Lewis Roca Rothgerber Christie LLP

(57) ABSTRACT

A system and method for detecting tumors. Three-dimensional scans of a patient are performed with penetrating radiation, before and/or after the injection of a contrast agent. Raw density arrays are formed from the scans. The median density within an organ is calculated and subtracted from each of the raw density arrays, to form offset arrays. The offset arrays are subtracted pairwise and the differences are summed to form a discriminator array.

20 Claims, 5 Drawing Sheets

(51) Int. Cl.
*G06T 7/40* (2017.01)
*G06T 7/11* (2017.01)
*G06T 5/50* (2006.01)
*A61B 6/00* (2006.01)
*A61B 6/03* (2006.01)

(52) U.S. Cl.
CPC ............... *G06T 2207/20224* (2013.01); *G06T 2207/30056* (2013.01); *G06T 2207/30096* (2013.01)

(56) References Cited

U.S. PATENT DOCUMENTS

| | | | | |
|---|---|---|---|---|
| 8,265,357 | B2* | 9/2012 | Ramsing | G06K 9/00127 345/587 |
| 10,102,682 | B1* | 10/2018 | Samaniego | G06T 3/60 |
| 2004/0102905 | A1* | 5/2004 | Adorjan | C12Q 1/6883 702/20 |
| 2005/0232474 | A1 | 10/2005 | Wei et al. | |
| 2008/0026385 | A1* | 1/2008 | Sharma | C12Q 1/6886 435/6.14 |
| 2009/0129653 | A1* | 5/2009 | DeHority | A61B 6/4233 382/132 |
| 2010/0246922 | A1* | 9/2010 | Uchihara | G06T 5/004 382/132 |
| 2012/0207270 | A1* | 8/2012 | Flohr | A61B 6/4014 378/5 |
| 2012/0212598 | A1* | 8/2012 | Mowrey | A61B 3/0008 348/78 |
| 2013/0051676 | A1* | 2/2013 | Wehnes | G06K 9/4628 382/190 |
| 2014/0315732 | A1* | 10/2014 | Lobe | C12Q 1/6886 506/9 |
| 2015/0004717 | A1* | 1/2015 | McDevitt | G01N 35/00029 436/501 |
| 2015/0262359 | A1 | 9/2015 | Fujiwara et al. | |
| 2015/0339809 | A1 | 11/2015 | Ohishi | |
| 2016/0055632 | A1* | 2/2016 | Fu | G01N 21/274 382/129 |
| 2016/0080548 | A1* | 3/2016 | Erickson | H04M 1/72527 455/556.1 |
| 2017/0071562 | A1* | 3/2017 | Suzuki | A61B 6/5205 |
| 2018/0278868 | A1* | 9/2018 | Dawson | H04N 5/379 |

OTHER PUBLICATIONS

International Search Report for corresponding International Application No. PCT/US2018/046564, filed Aug. 13, 2018, International Search Report dated Oct. 18, 2018 and dated Oct. 25, 2018 (5 pgs.).
Written Opinion of the International Searching Authority for corresponding International Application No. PCT/US2018/046564, filed Aug. 13, 2018, Written Opinion of the International Searching Authority dated Oct. 25, 2018 (9 pgs.).

* cited by examiner $$\begin{bmatrix} T(1)-T(1) & T(2)-T(1) & T(3)-T(1) & T(4)-T(1) \\ T(1)-T(2) & T(2)-T(2) & T(3)-T(2) & T(4)-T(2) \\ T(1)-T(3) & T(2)-T(3) & T(3)-T(3) & T(4)-T(3) \\ T(1)-T(4) & T(2)-T(4) & T(3)-T(4) & T(4)-T(4) \end{bmatrix} = \begin{bmatrix} 0 & -29 & -53 & -51 \\ 29 & 0 & -24 & -21 \\ 53 & 24 & 0 & 2.1 \\ 51 & 22 & -2.1 & 0 \end{bmatrix}$$

*FIG. 3A*

$$\begin{bmatrix} N(1)-N(1) & N(2)-N(1) & N(3)-N(1) & N(4)-N(1) \\ N(1)-N(2) & N(2)-N(2) & N(3)-N(2) & N(4)-N(2) \\ N(1)-N(3) & N(2)-N(3) & N(3)-N(3) & N(4)-N(3) \\ N(1)-N(4) & N(2)-N(4) & N(3)-N(4) & N(4)-N(4) \end{bmatrix} = \begin{bmatrix} 0 & -7.7 & -4.3 & -8.1 \\ 7.7 & 0 & 3.4 & -0.33 \\ 4.3 & -3.4 & 0 & -3.8 \\ 8.1 & 0.33 & 3.8 & 0 \end{bmatrix}$$

*FIG. 3B*

SUBTRACTION ALGORITHM FOR
DETECTION OF TUMORS

CROSS-REFERENCE TO RELATED APPLICATION(S)

The present application claims priority to and the benefit of U.S. Provisional Patent Application Ser. No. 62/545,410, filed Aug. 14, 2017, entitled "SUBTRACTION ALGORITHM FOR DETECTION OF TUMORS", the entire content of which is incorporated herein by reference.

The present application is related to U.S. patent application Ser. No. 15/489,652, filed on Apr. 17, 2017 entitled "SYSTEM AND METHOD FOR COMBINING 3D IMAGES IN COLOR", the entire content of which is incorporated herein by reference.

FIELD

One or more aspects of embodiments according to the present invention relate to systems and methods for detecting tumors, and more particularly to an algorithm for detecting tumors in computerized axial tomography scan data.

BACKGROUND

Computerized axial tomography scans may be used to obtain images of internal organs of patients, and such images may show indications of abnormalities, such as tumors, in a patient. These indications may be subtle, however, resulting in a risk of failing to diagnose abnormalities that are present, or of incorrectly concluding that abnormalities are present in a normal organ.

Thus, there is a need for an improved system and method of detecting tumors.

SUMMARY

Aspects of embodiments of the present disclosure are directed toward a system and method for detecting tumors. Three-dimensional scans of a patient are performed with penetrating radiation, before and/or after the injection of a contrast agent. Raw density arrays are formed from the scans. The median density within an organ is calculated and subtracted from each of the raw density arrays, to form offset arrays. The offset arrays are subtracted pairwise and the differences are summed to form a discriminator array.

According to an embodiment of the present invention there is provided a method for detecting a tumor, the method including: determining, in each of a plurality of raw density arrays, a respective median value within a region of the respective raw density array, each of the plurality of raw density arrays being a three dimensional array having a plurality of array elements, each of the raw density arrays being associated with a respective point in time, each element of each of the raw density arrays representing a density of a portion of a patient at the respective point in time; forming a plurality of offset density arrays, each corresponding to a respective one of the raw density arrays, the forming of the offset density arrays including subtracting, from each of the raw density arrays, the respective median value; forming a first difference array, the forming of the first difference array including subtracting, from a first offset density array, a second offset density array, the second offset density array being associated with a later point in time than the first offset density array; forming a second difference array, the forming of the second difference array including subtracting, from a third offset density array, a fourth offset density array, the fourth offset density array being associated with a later point in time than the third offset density array; and forming a discriminator array, the forming of the discriminator array including adding the first difference array and the second difference array.

In one embodiment, the method includes receiving the plurality of density arrays, each of the plurality of density arrays being an array of density values representing radiographic density in the patient.

In one embodiment, the forming of the discriminator array further includes replacing with zero any value that is less than zero, in each of the first difference array and the second difference array.

In one embodiment, the first offset density array is the same as the third offset density array.

In one embodiment, the method includes forming a plurality of difference arrays including the first difference array and the second difference array and including a difference array for every pair of offset density arrays, each of the difference arrays being formed by subtracting, from an earlier offset density array, a later offset density array, the later offset density array being associated with a later point in time than the earlier offset density array.

In one embodiment, the method includes an earliest raw density array associated with an earliest point in time and three later raw density arrays each associated with a point in time later than the earliest point in time, the three respective points in time associated with the three later raw density arrays being separated by about 30 seconds.

In one embodiment, the method includes: performing a first computerized axial tomography scan on a patient to obtain a first raw density array of the plurality of raw density arrays; injecting a contrast agent into the patient; and performing a second computerized axial tomography scan on the patient, about 30 seconds after injecting the contrast agent into the patient to obtain a second raw density array of the plurality of raw density arrays.

In one embodiment, the object is a patient and the region corresponds to an organ of the patient.

In one embodiment, the forming the discriminator array further includes setting to zero each element corresponding to a voxel that is not in the organ.

In one embodiment, the method includes displaying a two dimensional view of the discriminator array on a display.

In one embodiment, the forming the discriminator array further includes setting to zero each element of the discriminator array for which: a corresponding element of a difference array formed by subtracting, from an earliest offset density array of the plurality of offset density arrays, a second-earliest offset density array of the plurality of offset density arrays is less than or equal to zero; and a corresponding element of the second-earliest offset density array is less than 0, wherein the earliest offset density array is formed from a raw density array, of the plurality of raw density arrays, associated with an earliest one of the points in time, and the second-earliest offset density array is formed from a raw density array, of the plurality of raw density arrays, associated with a second-earliest one of the points in time.

In one embodiment, the forming the discriminator array further includes setting to zero each element of the discriminator array for which, for any of the raw density arrays, a corresponding element has a value greater than an upper threshold or less than a lower threshold.

According to an embodiment of the present invention there is provided a system for detecting a tumor, the system including: a scanner for scanning the object with penetrating radiation and measuring the transmission of the penetrating radiation through a patient; a processing circuit; and a display, the processing circuit being configured to: determine, in each of a plurality of raw density arrays, a respective median value within a region of the respective raw density array, each of the plurality of raw density arrays being a three dimensional array having a plurality of array elements, each of the density arrays being associated with a point in time, each element of each of the raw density arrays representing a density of a portion of a patient at the respective point in time; form a plurality of offset density arrays, each corresponding to a respective one of the raw density arrays, the forming of the offset density arrays including subtracting, from each of the raw density arrays, the respective median value; form a first difference array, the forming of the first difference array including subtracting, from a first offset density array, a second offset density array, the second offset density array being associated with a later point in time than the first offset density array; form a second difference array, the forming of the second difference array including subtracting, from a third offset density array, a fourth offset density array, the fourth offset density array being associated with a later point in time than the third offset density array; and form a discriminator array, the forming of the discriminator array including adding the first difference array and the second difference array.

In one embodiment, the forming of the discriminator array further includes replacing with zero any value that is less than zero, in each of the first difference array and the second difference array.

In one embodiment, the first offset density array is the same as the third offset density array.

In one embodiment, the system includes the first difference array and the second difference array and including a difference array for every pair of offset density arrays, each of the difference arrays being formed by subtracting, from an earlier offset density array, a later offset density array, the later offset density array being associated with a later point in time than the earlier offset density array.

In one embodiment, the system includes an earliest raw density array associated with an earliest point in time and three later raw density arrays each associated with a point in time later than the earliest point in time, the three respective points in time associated with the three later raw density arrays being separated by about 30 seconds.

In one embodiment, the object is a patient and the region corresponds to an organ of the patient.

In one embodiment, the forming the discriminator array further includes setting to zero each element corresponding to a voxel that is not in the organ.

In one embodiment, the forming the discriminator array further includes setting to zero each element of the discriminator array for which: a corresponding element of a difference array formed by subtracting, from an earliest offset density array of the plurality of offset density arrays, a second-earliest offset density array of the plurality of offset density arrays is less than or equal to zero; and a corresponding element of the second-earliest offset density array is less than 0, wherein the earliest offset density array is formed from a raw density array, of the plurality of raw density arrays, associated with an earliest one of the points in time, and the second-earliest offset density array is formed from a raw density array, of the plurality of raw density arrays, associated with a second-earliest one of the points in time.

BRIEF DESCRIPTION OF THE DRAWINGS

Features, aspects, and embodiments are described in conjunction with the attached drawings, in which:

FIG. 3A is an equation showing pairwise differences, arranged in a matrix, according to an embodiment of the present invention;

FIG. 3B is an equation showing pairwise differences, arranged in a matrix, according to an embodiment of the present invention;

DETAILED DESCRIPTION

The detailed description set forth below in connection with the appended drawings is intended as a description of exemplary embodiments of a system and method for detecting tumors provided in accordance with the present invention and is not intended to represent the only forms in which the present invention may be constructed or utilized. The description sets forth the features of the present invention in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like elements or features.

A computerized axial tomography (CAT or CT) scan is a procedure in which an object (e.g., a patient) is illuminated from several directions with penetrating (e.g., X-ray) radiation from a radiation source, and a raw scan image of the transmitted radiation is formed, in each instance, by a detector, to form a plurality of raw scan images, each of which may be represented as a two-dimensional array. The radiation may be attenuated at different rates in different kinds of matter; accordingly, each point in each image may correspond to a transmitted radiant intensity depending on the attenuation rates of the compositions of matter on the path along which the radiation traveled from the radiation source to the detector. From the combination of raw scan images a three-dimensional model of the "density", or "radiographic density", of the object may be formed, where, as used herein with respect to CAT scans, the "density" refers to the local rate of attenuation of the penetrating radiation. The density may be represented, for example, in Hounsfield units. Although examples are discussed in the present disclosure in the context of CAT scans of a human patient, the invention is not limited thereto, and in some embodiments other kinds of scans providing three-dimensional density data, such as magnetic resonance imaging scans, or positron emission tomography scans, or scans of objects other than human patients may be processed in an analogous fashion. In other embodiments, for example, another scanning method, that generates scans that are spatially registered in 3 dimensions to a sub-voxel level is used. In the case of other kinds of scans, density may be defined accordingly; in the case of a positron emission tomography scan, for example, the density may be the density of nuclei that decay by beta plus emission. As used herein, the term "object" includes anything that may be scanned, and encompasses without limitation human patients, animals, plants, inanimate objects, and combinations thereof.

Figure 1:
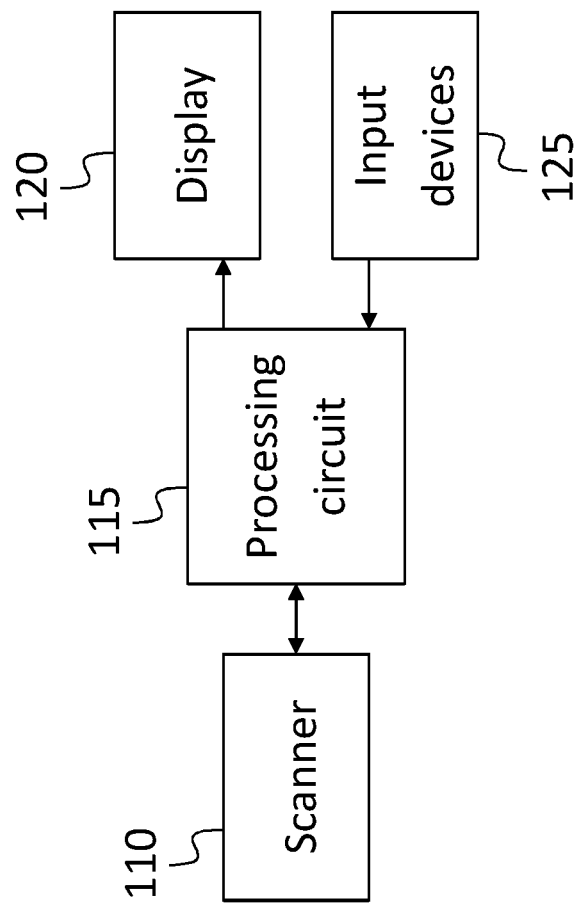
FIG. 1 is a system for detecting tumors, according to an embodiment of the present invention.

When the object being scanned is a human patient (or other living object), a contrast agent may be used (e.g., injected into or ingested by the patient) to selectively alter the density of some tissues. The contrast agent may for example include a relatively opaque substance (i.e., relatively opaque to the penetrating radiation). The density of tissue containing the contrast agent may be increased as a result, and it may be increased to an extent that depends on the concentration of contrast agent in the tissue. FIG. 1 shows a block diagram of a system for performing a scan and processing and displaying the results, according to one embodiment. The system includes a scanner 110, a processing circuit 115 (described in further detail below), a display 120 for displaying images, or sequences of images in the form of a movie, and one or more input devices 125 such as a keyboard or mouse, that an operator (e.g., a radiologist) may use to operate the system, and to set parameters affecting the processing of the images to be displayed. It should be noted that the processing circuit 115, display 120, and input devices 125 could be part of a unitary system or could be a distributed system, with the processing circuit 115, for example, being separate and communicatively coupled to the display 120 and input devices 125. In some embodiments servers store the images and clients request the stored images, with image processing performed on the server or on the client, or both.

A plurality of scans may be performed, and analyzed together. For example, a first scan may be performed before the contrast agent is injected, and several subsequent scans may be performed at various times (e.g., at regular intervals, such as 30-second intervals) after injection of the contrast agent, as the concentration of contrast agent changes. The rate at which the concentration of contrast agent increases initially, the peak concentration reached, and the rate at which the concentration of contrast agent subsequently decreases all may depend on the type of tissue.

Figure 2:
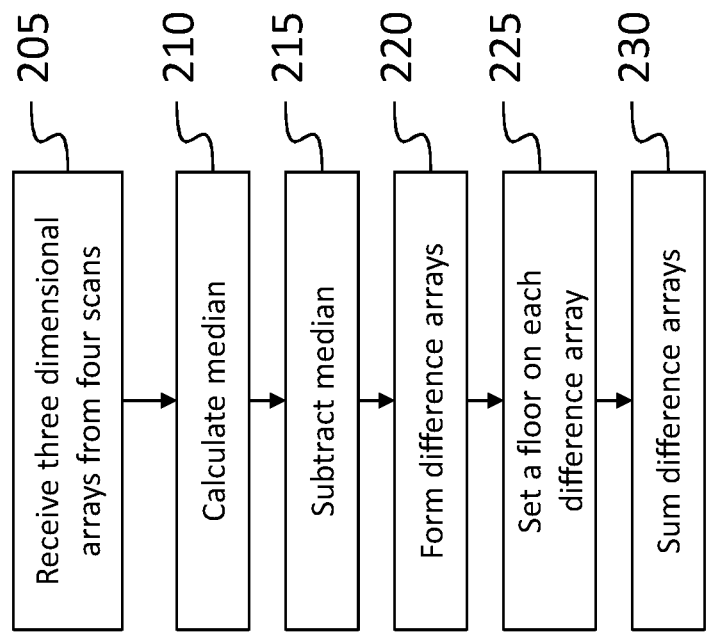
FIG. 2 is a flow chart of a method for detecting tumors, according to an embodiment of the present invention.

In some embodiments, various methods may be employed to generate images from CAT scan data to aid in the use of a CAT scan as a diagnostic tool. A sequence of steps, or "acts", illustrated in FIG. 2 and discussed in further detail below, may be used, for example, to enhance the difference in appearance between normal tissue and cancerous tissue (i.e., a malignant tumor). The process is illustrated, for a patient's liver, in FIG. 2 and in the sample code of Listing 1, below. In other embodiments, an analogous approach may be used to identify cancerous tissue in other organs.

Listing 1 shows MATLAB™ code for generating a discriminator array that may be used to detect a tumor, i.e., to determine whether a tumor is present in a patient. The code of Listing 1 receives, as input, the variables, a1, a2, a3, and a4, each of which contains a "raw density array" (e.g., a first raw density array, a second raw density array, a third raw density array, and a fourth raw density array). Each element of each raw density array represents the density of tissue in a small volume or "voxel" at a physical location in the patient corresponding to the coordinates of the element.

These (three-dimensional) raw density arrays may be generated (to then be received, in act 205 (FIG. 2)) from the (two-dimensional) raw scan images using, e.g., a deconvolution process to infer the density, in three dimensions, of the object (e.g., the patient) being scanned. The first variable, a1, may include data from a scan performed before a contrast agent was injected into the patient, and the remaining three files may include data from scans performed at intervals (e.g., 30 second intervals) after the contrast agent was injected into the patient. However, it should be understood that other timing intervals, or a different number of images, may be used.

In an act 210, the median, over the voxels corresponding to the patient's liver, within each of the raw density arrays, is calculated, and in an act 215 the median is subtracted from the respective raw density array. This act may be implemented, for example, by the code of lines 3-9 of Listing 1. In Listing 1, liver_mask is a mask that identifies voxels that are within the patient's liver. The liver mask is a list of element positions in a linearized representation of the raw density arrays. The variables a1, a2, a3, and a4 represent (as mentioned above) the raw density arrays, and a1m, a2m, a3m, and a4m are "offset density arrays", obtained by subtracting the respective medians, as shown in Listing 1. Each of the raw density arrays and each of the offset density arrays has associated with it a point in time at which the scan that resulted in the raw density array or the offset density array was performed. As such, within any pair of raw density arrays, one, the "earlier" raw density array resulted from a scan performed at an earlier time than the other, which may be referred to as the "later" raw density array. As such, the adjectives such as "earliest", "second-earliest", "earlier", and "later", when used herein to qualify a raw density array or an offset density array refer to the time at which the scan that resulted in the respective array was performed.

In an act 220, (implemented in lines 18-25 of Listing 1), difference arrays are formed by subtracting the offset density arrays from each other pair-wise. Each possible difference array is formed, so that for four scans (and, accordingly, for four offset density arrays), six difference arrays (i.e., four choose two or 4!/(2! 2!) difference arrays) are formed. These difference arrays are stored, as a result of the execution of lines 20-25 of Listing 1, in the six variables s12, s13, s14, s23, s24, and s34. Each difference array is the result of subtracting, from an earlier offset density array (i.e., an offset density array resulting from an earlier-performed scan), a later offset density array (i.e., an offset density array resulting from a later-performed scan). In some embodiments, more or fewer than four scans are used. In such a case more or fewer than six difference arrays may be calculated; if all possible pairwise differences are calculated, the number of difference arrays may be n choose 2 (i.e., n!/(n! 2!)) if n scans are used.

Conceptually, the six elements corresponding to a voxel in each of the six difference arrays may be considered to correspond to the lower triangular portion of an antisymmetric matrix (or "skew-symmetric" matrix) examples of which are illustrated in FIG. 3A (for tumorous tissue) and FIG. 3B (for normal tissue). In FIG. 3A, each T(i) is a value from one voxel of the offset density array from the $i^{th}$ scan of a sequence of four scans as described above, where the voxel is within tumorous tissue. In FIG. 3B, each N(i) is a value from one voxel of the offset density array from the $i^{th}$ scan of a sequence of four scans as described above, where the voxel is within normal tissue. As used herein, the "lower triangular portion" of a square matrix refers to the elements below the diagonal. Each off-diagonal element at coordinates (i, j) is calculated by subtracting a value from the $i^{th}$ scan from a value from the $j^{th}$ scan, where the values may be two voxels from the same positions in the offset density arrays corresponding to the two scans (as illustrated in FIGS. 3A and 3B), or the entire raw density arrays (as is the case for the code of lines 20-25 of Listing 1). The matrix of FIG. 3A is numerically not precisely skew-symmetric because of rounding error.

Figure 4A:
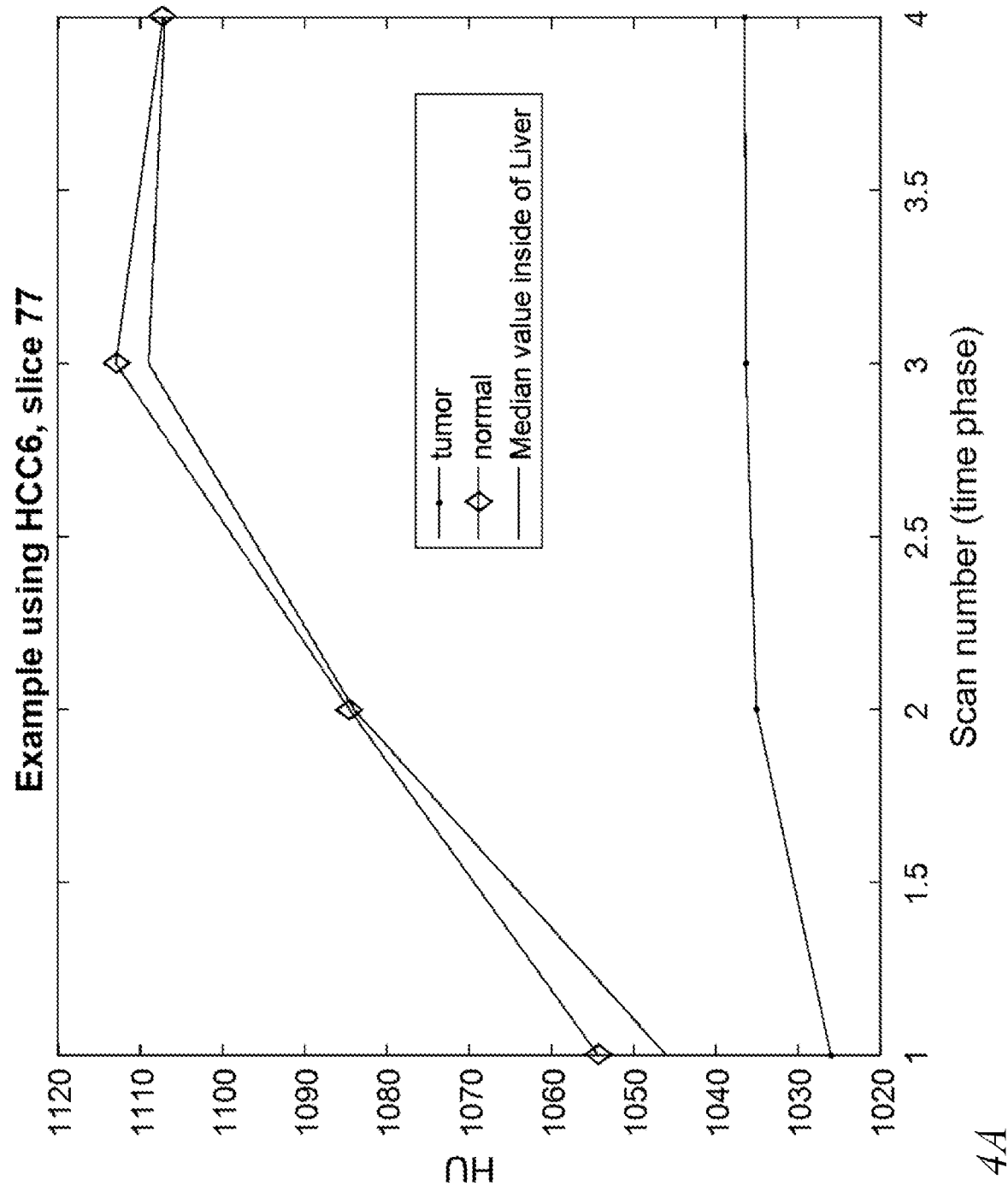
FIG. 4A is a graph of density as a function of time, according to an embodiment of the present invention.
Figure 4B:
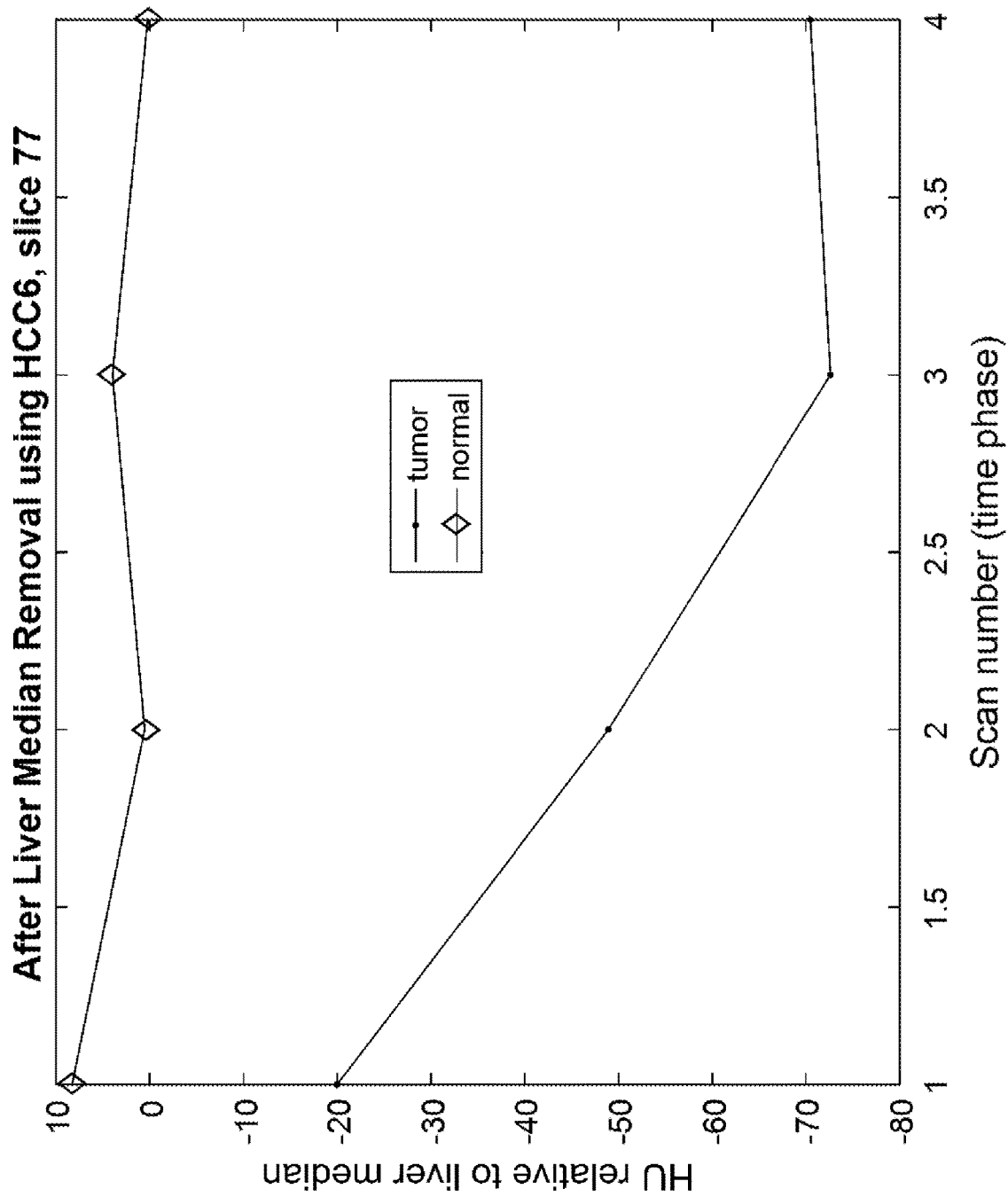
FIG. 4B is a graph of density as a function of time, according to an embodiment of the present invention.

FIGS. 4A and 4B show similar results graphically, each being a graph of density in Hounsfield units as a function of time. Raw scan data are shown in FIG. 4A, and offset data (i.e., density after subtraction of the median value for the liver) are shown in FIG. 4B. In a liver consisting primarily of normal tissue, the median density may correspond to the density of normal tissue; accordingly, subtracting the median value (the result of which is shown in FIG. 4B) may result in little variation in the offset data for normal tissue, and the variation, in the offset data, may be more pronounced for tumorous tissue than it is in the raw data.

A floor may then be set at zero, in an act 225; in each of the difference arrays (each of which includes elements corresponding to one of the elements of the lower triangular portion of a matrix such as that of FIG. 3A or of FIG. 3B), elements that are less than zero may be replaced with zero. In an act 230, the difference arrays (after the setting of the floor at zero) are summed. This summation is implemented on line 34 of Listing 1 (line 34 begins with "imgData=" and ends with " . . . "). The sum may be a tumor indicator, or a discriminator array, i.e., a result that generally takes a relatively high value for voxels within tumorous tissue and a relatively low value for voxels in normal tissue.

Further steps may be taken to improve the ability of the discriminator to produce images in which tumorous tissue is highlighted while reducing the likelihood of generating false alarms, i.e., the likelihood of highlighting normal tissue. For example, as shown in lines 11-16 and 35, a data masking array (data_mask in Listing 1), in which each element has (i) a value of zero if the corresponding element of any of the raw density arrays has a value exceeding an upper threshold or less than a lower threshold and (ii) a value of one otherwise, may be formed and multiplied (as, e.g., in line 35 of Listing 1) by the discriminator array. The upper and lower thresholds may be set to correspond to the range of densities expected for the organ of interest, and this method may be used to identify voxels that are not part of the organ of interest. For example, if due to an error in the definition of a mask for the liver (liver_mask in Listing 1) some bone is present in the region defined by the liver mask, and if bone has a significantly higher density than liver tissue, then the raw density arrays may have values exceeding the upper threshold in the elements corresponding to voxels containing bone, and the corresponding elements of the data masking array may be set to zero, resulting in the corresponding elements of the discriminator array being set to zero.

A pattern mask (pattern_mask in Listing 1) may further be used to set to zero elements that have characteristics indicating a likelihood of false alarm. Listing 1 shows a test for such characteristics on line 29. Each element of the pattern mask is (i) set to zero when the corresponding element of the difference array formed by subtracting the second-earliest offset density array from the earliest offset density array has a value less than or equal to zero and the corresponding element of the second-earliest offset density array has a value less than zero, and (ii) set to one otherwise. This pattern mask is used in line 35 of Listing 1 to set to zero each element of the discriminator array for which the pattern mask is zero.

The discriminator array may be displayed to an operator (e.g., a radiologist) who may then make a determination regarding whether a tumor appears to be present in the patient. The discriminator array may be displayed as a moving display that simulates the patient being rotated in front of the operator, with the image of the patient being partially transparent and with the discriminator being displayed, for example, as the intensity of one color (e.g., red) in a three-color (e.g., red, green blue) display. The code of Listing 2 (which calls the ordfilt3 function defined in Listing 3) generates an example of such a moving display. In other embodiments, the discriminator array (a three dimensional array) may be displayed as a sequence of two-dimensional slices. The code of Listing 4 (which also calls the ordfilt3 function defined in Listing 3) generates an array of such slices, in an exemplary embodiment.

Listing 1

```
1  % Core cumulative subtraction matrix algorithm
2
3  % First remove the liver median from each scan
4  % Since the median is an estimate of a healthy liver tissue value,
5  % this should "flatten" the response of healthy tissue
6  a1m = a1 - median(a1(liver_mask));
7  a2m = a2 - median(a2(liver_mask));
8  a3m = a3 - median(a3(liver_mask));
9  a4m = a4 - median(a4(liver_mask));
10
11 % data mask is a logical array that will discard (0) anything outside of
12 % expected values for the liver
13 data_mask = a1>mask_lower_scan_thr &
   a1<mask_upper_scan_thr & ...
14    a2>mask_lower_scan_thr & a2<mask_upper_scan_thr & ...
15    a3>mask_lower_scan_thr & a3<mask_upper_scan_thr & ...
16    a4>mask_lower_scan_thr & a4<mask_upper_scan_thr;
17
18 % compute all 6 combinations of early time minus late time
19 % CSMA lower triangular
20 s12 = a1m-a2m;
21 s13 = a1m-a3m;
22 s14 = a1m-a4m;
23 s23 = a2m-a3m;
24 s24 = a2m-a4m;
25 s34 = a3m-a4m;
26
27 % pattern mask is a logical that will zero out certain patterns that were
28 % deemed to be false alarms
29 pattern_mask = single(s12 > 0) + single(s12 <= 0).*single(a2m < 0);
30
31 % final result accumulates the greater of 0 and the 6 matrix terms and
   also
32 % applies the masks (liver mask is passed in and is 1 inside the liver,
   and
33 % 0 outside the liver)
   imgData =
34 (max(s12,0)+max(s13,0)+max(s14,0)+max(s23,0)+max(s24,0)+
   max(s34,0)) ...
35    .*single(liver_mask).*data_mask.*pattern_mask;
```

Listing 2

```
1  % Make a gray 3D image (movie) using scans and overlay with various methods
2  % of cancer detection in Red
3
4  crop_to_liver_en = 0;
5  erode_livermask_en = 1;
6  mask_lower_scan_thr = 900;
```

-continued

Listing 2

```
 7 mask_upper_scan_thr = 1200;
 8
 9 sub_fract = 1.0;
10 fudge=20;
11 bias = fudge-50 - (1-sub_fract)*1000;
12
13 c1 = 1;
14 c2 = 1;
15 c3 = 1;
16 gain = 0.333;
17
18 G = 11.25 * 1.5; % 0.5=low, 1=medium, 1.5=high, 2=very high
19
20 ROTXY = 1;
21 ROTXZ = 2;
22 ROTYZ = 3;
23
24 rot_axis = ROTXY;
25
26 dirname = 'H:\Apollo\data\ROC Curve Data\';
27
28 if ~exist('c_type','var')
29    c_type = input('c_type (hcc, pancreas_data):','s');
30 end
31
32 if ~exist('patient_num','var')
33    patient_num = input('Patient number:');
34 end
35
36 fname = strcat( dirname,c_type'\',num2str(patient_num);'_imgset1.mat');
37
38 load(fname)
39
40 % Peter's liver masks
41 load(strcat(dirname,c_type,'\livermask_',c_type,'_',num2str(patient_num);'mat'))
42 if erode_livermask_en
43    liver_mask = bw_eroded;
44 else
45    liver_mask = bw;
46 end
47
48 a1 = single(imgset1(1).image);
49 a2 = single(imgset1(2).image);
50 a3 = single(imgset1(3).image);
51 a4 = single(imgset1(4).image);
52
53 if max(liver_mask(:)) > 0 && size(a1,3)==size(liver_mask,3)
54
55    %-------------------------------------------------------------------
56    %-------------------------------------------------------------------
57    core_csma
58    %-------------------------------------------------------------------
59    %-------------------------------------------------------------------
60
61    e = imgData/600;
62
63    e = ordfilt3( e, 5,5,3);
64    % Square decompresses covariance values but still in -1 to 1 range
65    e = e.^2; % .* sign(imgData);
66
67    grscl = a2-sub_fract*a1;
68
69    bkg = mean(grscl(liver_mask==1));
70
71    a21 = grscl + G*e/0.3*bkg;
72    a31 = grscl;
73    a41 = grscl;
74
75    idx_offset=0;
76
77    liv_cut_x = max(squeeze(max(liver_mask,[ ],3)),[ ],2);
78    x_idx_liv = find(liv_cut_x > 0.5);
79    liv_cut_y = max(squeeze(max(liver_mask,[ ],3)),[ ],1);
80    y_idx_liv = find(liv_cut_y > 0.5);
81    liv_cut_z = max(squeeze(max(liver_mask,[ ],1)),[ ],1);
82    z_idx_liv = find(liv_cut_z > 0.5);
83
```

-continued

| Listing 2 |

```
84    if crop_to_liver_en
85        a21 = a21( x_idx_liv, y_idx_liv, z_idx_liv);
86        a31 = a31( x_idx_liv, y_idx_liv, z_idx_liv);
87        a41 = a41( x_idx_liv, y_idx_liv, z_idx_liv);
88        liver_mask = liver_mask( x_idx_liv, y_idx_liv, z_idx_liv);
89    end
90
91    red4 = max(a21+bias,eps).*liver_mask;
92    grn4 = max(a31+bias,eps).*liver_mask;
93    blu4 = max(a41+bias,eps).*liver_mask;
94
95    red5 = red4;
96    grn5 = grn4;
97    blu5 = blu4;
98
99    [Nx,Ny,Nz] = size(red5);
100
101   if rot_axis == ROTXZ
102       mask = ones(Nx,1) * (1:Nz).^2;
103   elseif rot_axis == ROTYZ
104       mask = ones(Ny,1) * (1:Nz).^2;
105   elseif rot_axis == ROTXY
106       mask = (Nx:-1:1)'.^3/Nx^2 * ones(1,Ny);
107   end
108
109   ANG_LIMIT = 90;
110
111   ANG_STEP = round( ANG_LIMIT/45);
112
113   ang_array = [(0:-ANG_STEP:-ANG_LIMIT),...
114       (-ANG_LIMIT+1:ANG_STEP:ANG_LIMIT),(ANG_LIMIT-1:-ANG_STEP:1)];
115
116   clear col_im
117   clear Mov
118
119   img_count = 0;
120
121   for ang = 0 %ang_array
122
          for n = 1 : Ny*(rot_axis==ROTXZ) + Nx*(rot_axis==ROTYZ) +
123   Nz*(rot_axis==ROTXY)
124
125           if rot_axis == ROTXZ
126               red_temp = squeeze( red4(:,n,:) );
127               grn_temp = squeeze( grn4(:,n,:) );
128               blu_temp = squeeze( blu4(:,n,:) );
129           elseif rot_axis == ROTYZ
130               red_temp = squeeze( red4(n,:,:) );
131               grn_temp = squeeze( grn4(n,:,:) );
132               blu_temp = squeeze( blu4(n,:,:) );
133           elseif rot_axis == ROTXY
134               red_temp = squeeze( red4(:,:,n) );
135               grn_temp = squeeze( grn4(:,:,n) );
136               blu_temp = squeeze( blu4(:,:,n) );
137           end
138
139           red_tempr=imrotate(red_temp,ang,'nearest','crop');
140           grn_tempr=imrotate(grn_temp,ang,'nearest','crop');
141           blu_tempr=imrotate(blu_temp,ang,'nearest','crop');
142
143           if rot_axis == ROTXZ
144               red5(:,n,:) = red_tempr .* mask;
145               grn5(:,n,:) = grn_tempr .* mask;
146               blu5(:,n,:) = blu_tempr .* mask;
147           elseif rot_axis == ROTYZ
148               red5(n,:,:) = red_tempr .* mask;
149               grn5(n,:,:) = grn_tempr .* mask;
150               blu5(n,:,:) = blu_tempr .* mask;
151           elseif rot_axis == ROTXY
152               red5(:,:,n) = red_tempr .* mask;
153               grn5(:,:,n) = grn_tempr .* mask;
154               blu5(:,:,n) = blu_tempr .* mask;
155           end
156       end
```

Listing 2

```
157
158    siz1 = 512; %size(red5,1); %max( size(red5,1), 886/2); %886;
159
160    if rot_axis == ROTXZ || rot_axis == ROTYZ
161       red_im = squeeze(c1*mean(red5,3)+c2*max(red5,[ ],3)+c3*std(red5,[ ],3));
162       grn_im = squeeze(c1*mean(grn5,3)+c2*max(grn5,[ ],3)+c3*std(grn5,[ ],3));
163       blu_im = squeeze(c1*mean(blu5,3)+c2*max(blu5,[ ],3)+c3*std(blu5,[ ],3));
164       fctr = siz1/(size(red_im,1));
165    elseif rot_axis == ROTXY
166       red_im = squeeze(c1*mean(red5,1)+c2*max(red5,[ ],1)+c3*std(red5,[ ],1))';
167       grn_im = squeeze(c1*mean(grn5,1)+c2*max(grn5,[ ]1)+c3*std(grn5,[ ],1))';
168       blu_im = squeeze(c1*mean(blu5,1)+c2*max(blu5,[ ],1)+c3*std(blu5,[ ],1))';
169       fctr = siz1/(size(red_im,1)*2.5);
170    end
171
172    siz2 = round(fctr*size(red_im,2));
173    if siz2 > 1700
174       siz2 = 1700;
175       siz1 = round(siz2*(size(red_im,1)*2.5)/size(red_im,2));
176    end
177    col_im(:,:,1) = imresize(red_im,[siz1,siz2],'bilinear');
178    col_im(:,:,2) = imresize(grn_im,[siz1,siz2],'bilinear');
179    col_im(:,:,3) = imresize(blu_im,[siz1,siz2],'bilinear');
180    denom = mean(blu_im(blu_im>eps));
181
182    image(max(0,min(1,gain*col_im/denom)))
183    if img_count==0,truesize;end
184
185    img_count = img_count + 1;
186
187    axis('image','off')
188
189    drawnow
190    Mov(img_count)=getframe;
191
192    end
193
194
195    fname_avi = strcat( fname(1:strfind(fname,'_imgset1')),c_type,'_csma_3D.avi');
196
197    movie2avi1( Mov, fname_avi, 30)
198
199 end
```

Listing 3

```
1  function a_filt = ordfilt3( a, NFILTx, NFILTy, NFILTz )
2
3  %median filter in x-y
4  %min filter in z
5
6  xyfilt_order = 0.5; %0.5 = median
7
8  a_filt = a;
9
10 [~,~,Nz] = size(a);
11
12 for z = 1 : Nz
13
14    if NFILTx>1 || NFILTy>1
       a_filt(:,:,z) =
15 ordfilt2(squeeze(a(:,:,z)),round(NFILTx*NFILTy*xyfilt_order),
   ones(NFILTx,NFILTy));
16    end
17
18 end
19
20 temp = a_filt;
21
22 if NFILTz>1
23    for z = (NFILTz+1)/2 : Nz-(NFILTz-1)/2
24       a_filt(:,:,z) = median( temp(:,:,z-(NFILTz-1)/
          2:z+(NFILTz-1)/2),3);
```

Listing 3 -continued

```
25 %    a_filt(:,:,z) = min( temp(:,:,z-(NFILTz-1)/
         2:z+(NFILTz-1)/2),[ ],3);
26    end
27 end
```

Listing 4

```
1  % clear
2  % close all
3
4  % Magic numbers
5  erode_livermask_en = 1;
6  mask_lower_scan_thr = 900;
7  mask_upper_scan_thr = 1200;
8  disp_lower_scan_thr = 900;
9  disp_upper_scan_thr = 1300;
10 scale_factor1 = 0.5;
11 scale_factor2 = 0.375;
12 imgData_norm = 600;
13 L_med_x = 5;
14 L_med_y = 5;
15 L_med_z = 3;
16 e_power = 2;
17 contrast_setting = 1.5; %0.5=LO, 1=MED, 1.5=HI, 2= VHI
```

Listing 4 -continued

```
18  G = 100 * contrast_setting;
19
20  if ~exist('c_type','var')
21     c_type = input('c_type (hcc, pancreas_data):','s');
22  end
23
24  if ~exist('patient_num','var')
25     patient_num = input('Patient number:');
26  end
27
28  dirname = 'h:\apollo\data\ROC Curve Data\';
29
30  fname = strcat( dirname,c_type.'\',num2str(patient_num);
    '_imgset1.mat');
31  load(fname)
32
33  clear bw
34  clear BW
35
36  load(strcat(dirname,c_type,'\livermask_',c_type,
    '_',num2str(patient_num);'.mat'))
37
38  if erode_livermask_en
39     liver_mask = bw_eroded;
40  else
41     liver_mask = bw;
42  end
43
44  num_scans = length(imgset1);
45  num_slices = size(imgset1(1).image,3);
46
47  % fprintf('Number of scans = %i\n',num_scans)
48  % fprintf('Number of slices = %i\n',num_slices)
49
50  a1 = single(imgset1(1).image);
51  a2 = single(imgset1(2).image);
52  a3 = single(imgset1(3).image);
53  a4 = single(imgset1(4).image);
54
55  if length(liver_mask(:)) == length(a1(:))
56
57    %-----------------
58    %-----------------
59    core_csma
60    %-----------------
61    %-----------------
62
63    %-----------------
64    %-----------------
65    %-----------------
66    % DISPLAY CUBE CODE below
67    %-----------------
68    %-----------------
69    %-----------------
70
71    e = imgData/imgData_norm;
72    e = ordfilt3( e, L_med_x,L_med_y,L_med_z);
73    e = e.^e_power;
74
     grscl = max(0,
       min(disp_upper_scan_thr-disp_lower_scan_thr,a2-
75   disp_lower_scan_thr));
76
77    bkg = mean(grscl(liver_mask==1));
78
79    % add "e" to red only
80    a21 = grscl + G*e*bkg;
81    a31 = grscl;
82    a41 = grscl;
83
84    red4 = max(a21,eps).*liver_mask;
85    grn4 = max(a31,eps).*liver_mask;
86    blu4 = max(a41,eps).*liver_mask;
87
88    data = zeros(size(a21,1),size(a21,2),size(a21,3),3,'single');
89    norm_fact = 3*median(grn4(liver_mask == 1));
90
91    data(:,:,:,1) = red4/norm_fact*scale_factor2;
92    data(:,:,:,2) = grn4/norm_fact*scale_factor2;
93    data(:,:,:,3) = blu4/norm_fact*scale_factor2;
94
95    csma = uint8( round( 255*min(1,max(0,data))));
96
      fname_mat = strcat(
97  fname(1:strfind(fname,'_imgset1')),c_type,'_csma_4D.mat');
98
99    save(fname_mat,'csma')
100
101 else
102
103    fprintf('Error: Liver mask has z dimension %i\n',
         size(liver_mask,3))
104 end
```

The term "processing circuit" is used herein to include any combination of hardware, firmware, and software, employed to process data or digital signals. Processing circuit hardware may include, for example, application specific integrated circuits (ASICs), general purpose or special purpose central processing units (CPUs), digital signal processors (DSPs), graphics processing units (GPUs), and programmable logic devices such as field programmable gate arrays (FPGAs). In a processing circuit, as used herein, each function is performed either by hardware configured, i.e., hard-wired, to perform that function, or by more general purpose hardware, such as a CPU, configured to execute instructions stored in a non-transitory storage medium. A processing circuit may be fabricated on a single printed wiring board (PWB) or distributed over several interconnected PWBs. A processing circuit may contain other processing circuits; for example a processing circuit may include two processing circuits, an FPGA and a CPU, interconnected on a PWB. A processing circuit may include a plurality of processing units that are geographically separated, and connected, e.g., by a network such as the internet.

Although limited embodiments of a system and method for detecting tumors have been specifically described and illustrated herein, many modifications and variations will be apparent to those skilled in the art. Accordingly, it is to be understood that the system and method for detecting tumors employed according to principles of this invention may be embodied other than as specifically described herein. The invention is also defined in the following claims, and equivalents thereof.

What is claimed is:

1. A method for detecting a tumor, the method comprising:
    determining, in each of a plurality of raw density arrays, a respective median value within a region of the respective raw density array, each of the plurality of raw density arrays being a three dimensional array having a plurality of array elements, each of the raw density arrays being associated with a respective point in time, each element of each of the raw density arrays representing a density of a portion of a patient at the respective point in time;
    forming a plurality of offset density arrays, each corresponding to a respective one of the raw density arrays, the forming of the offset density arrays comprising subtracting, from each of the raw density arrays, the respective median value;
    forming a first difference array, the forming of the first difference array comprising subtracting, from a first offset density array, a second offset density array, the second offset density array being associated with a later point in time than the first offset density array;

forming a second difference array, the forming of the second difference array comprising subtracting, from a third offset density array, a fourth offset density array, the fourth offset density array being associated with a later point in time than the third offset density array; and forming a discriminator array, the forming of the discriminator array comprising adding the first difference array and the second difference array.

2. The method of claim 1, further comprising receiving the plurality of density arrays, each of the plurality of density arrays being an array of density values representing radiographic density in the patient.

3. The method of claim 1, wherein the forming of the discriminator array further comprises replacing with zero any value that is less than zero, in each of the first difference array and the second difference array.

4. The method of claim 1, wherein the first offset density array is the same as the third offset density array.

5. The method of claim 1, further comprising forming a plurality of difference arrays including the first difference array and the second difference array and including a difference array for every pair of offset density arrays, each of the difference arrays being formed by subtracting, from an earlier offset density array, a later offset density array, the later offset density array being associated with a later point in time than the earlier offset density array.

6. The method of claim 1, wherein the plurality of raw density arrays consists of four raw density arrays, including an earliest raw density array associated with an earliest point in time and three later raw density arrays each associated with a point in time later than the earliest point in time, the three respective points in time associated with the three later raw density arrays being separated by about 30 seconds.

7. The method of claim 1, further comprising:
performing a first computerized axial tomography scan on a patient to obtain a first raw density array of the plurality of raw density arrays;
injecting a contrast agent into the patient; and
performing a second computerized axial tomography scan on the patient, about 30 seconds after injecting the contrast agent into the patient to obtain a second raw density array of the plurality of raw density arrays.

8. The method of claim 1, wherein the object is a patient and the region corresponds to an organ of the patient.

9. The method of claim 8, wherein the forming the discriminator array further comprises setting to zero each element corresponding to a voxel that is not in the organ.

10. The method of claim 1, further comprising displaying a two dimensional view of the discriminator array on a display.

11. The method of claim 1, wherein the forming the discriminator array further comprises setting to zero each element of the discriminator array for which:
a corresponding element of a difference array formed by subtracting,
from an earliest offset density array of the plurality of offset density arrays,
a second-earliest offset density array of the plurality of offset density arrays
is less than or equal to zero; and
a corresponding element of the second-earliest offset density array is less than 0,
wherein the earliest offset density array is formed from a raw density array, of the plurality of raw density arrays, associated with an earliest one of the points in time, and the second-earliest offset density array is formed from a raw density array, of the plurality of raw density arrays, associated with a second-earliest one of the points in time.

12. The method of claim 1, wherein the forming the discriminator array further comprises setting to zero each element of the discriminator array for which, for any of the raw density arrays, a corresponding element has a value greater than an upper threshold or less than a lower threshold.

13. A system for detecting a tumor, the system comprising:
a scanner for scanning the object with penetrating radiation and measuring the transmission of the penetrating radiation through a patient;
a processing circuit; and
a display,
the processing circuit being configured to:
determine, in each of a plurality of raw density arrays, a respective median value within a region of the respective raw density array, each of the plurality of raw density arrays being a three dimensional array having a plurality of array elements, each of the density arrays being associated with a point in time, each element of each of the raw density arrays representing a density of a portion of a patient at the respective point in time;
form a plurality of offset density arrays, each corresponding to a respective one of the raw density arrays, the forming of the offset density arrays comprising subtracting, from each of the raw density arrays, the respective median value;
form a first difference array, the forming of the first difference array comprising subtracting, from a first offset density array, a second offset density array, the second offset density array being associated with a later point in time than the first offset density array;
form a second difference array, the forming of the second difference array comprising subtracting, from a third offset density array, a fourth offset density array, the fourth offset density array being associated with a later point in time than the third offset density array; and
form a discriminator array, the forming of the discriminator array comprising adding the first difference array and the second difference array.

14. The system of claim 13, wherein the forming of the discriminator array further comprises replacing with zero any value that is less than zero, in each of the first difference array and the second difference array.

15. The system of claim 13, wherein the first offset density array is the same as the third offset density array.

16. The system of claim 13, wherein the processing circuit is further configured to form a plurality of difference arrays including the first difference array and the second difference array and including a difference array for every pair of offset density arrays, each of the difference arrays being formed by subtracting, from an earlier offset density array, a later offset density array, the later offset density array being associated with a later point in time than the earlier offset density array.

17. The system of claim 13, wherein the plurality of raw density arrays consists of four raw density arrays, including an earliest raw density array associated with an earliest point in time and three later raw density arrays each associated with a point in time later than the earliest point in time, the three respective points in time associated with the three later raw density arrays being separated by about 30 seconds.

18. The system of claim 13, wherein the object is a patient and the region corresponds to an organ of the patient.

19. The system of claim 18, wherein the forming the discriminator array further comprises setting to zero each element corresponding to a voxel that is not in the organ.

20. The method of claim 13, wherein the forming the discriminator array further comprises setting to zero each element of the discriminator array for which:
   a corresponding element of a difference array formed by subtracting,
      from an earliest offset density array of the plurality of offset density arrays,
      a second-earliest offset density array of the plurality of offset density arrays
      is less than or equal to zero; and
   a corresponding element of the second-earliest offset density array is less than 0,
   wherein the earliest offset density array is formed from a raw density array, of the plurality of raw density arrays, associated with an earliest one of the points in time, and the second-earliest offset density array is formed from a raw density array, of the plurality of raw density arrays, associated with a second-earliest one of the points in time.

* * * * *